US00PP25091P3

(12) United States Plant Patent
Zaiger et al.

(10) Patent No.: US PP25,091 P3
(45) Date of Patent: Nov. 25, 2014

(54) INTERSPECIFIC TREE NAMED 'BELLA SWEET'

(50) Latin Name: ***Interspecific Prunus* species**
Varietal Denomination: Bella Sweet

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/986,289

(22) Filed: Apr. 19, 2013

(65) Prior Publication Data

US 2014/0317794 P1 Oct. 23, 2014

(51) Int. Cl.
*A01H 5/08* (2006.01)

(52) U.S. Cl.
USPC ..... Plt./180

(58) Field of Classification Search
CPC ..... A01H 5/00; A01H 5/0862; A01H 5/0843; A01H 5/0868
USPC ..... Plt./180
See application file for complete search history.

*Primary Examiner* — June Hwu
*Assistant Examiner* — Keith Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Heavy and regular production of large size fruit.
3. Fruit with attractive red skin color.
4. Fruit with excellent flavor and eating quality.

1 Drawing Sheet

Botanical designation: Interspecific *Prunus* species.
Variety denomination: 'Bella Sweet'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and peach trees, which are known to us, and mentioned herein, 'Flavor Treat' Interspecific (U.S. Plant Pat. No. 12,936), 'Bella Royale' Interspecific (U.S. Plant Pat. No. 19,925), our non-patented proprietary interspecific selections '119LT340', '53MB152', '66Z352', '67Z1' and our proprietary peen-to peach selection '55ZA18' (non-patented).

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses of the following species; *Prunus salicina, Prunus armeniaca* and *Prunus persica*. The present variety is a first generation cross between our proprietary non-patented interspecific seedlings with the field identification numbers '119LT340' and '53MB152'. The seed parent (119LT340) interspecific (non-patented) originated as a first generation cross between our proprietary interspecific seedling '66Z352' (non-patented) and 'Flavor Treat' Interspecific (U.S. Plant Pat. No. 12,936). The pollen parent (53MB152) interspecific (non-patented) originated as a first generation cross between our proprietary non-patented interspecific seedling '67Z1' and our proprietary peen-to peach seedling '55ZA18' (non-patented). A large number of these first generation seedlings, growing on their own root system, were budded to older trees of 'Nemaguard' Rootstock (non-patented) to induce earlier fruit production for evaluation. Under close and careful observation, one seedling, which is the present variety, exhibited desirable fruit and tree characteristics and was selected in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree (Plum×Apricot×Peach) is of large size, vigorous, upright growth and a productive and regular bearer of large size, yellow flesh fruit with excellent flavor and eating quality. The fruit is further characterized by having attractive red skin that has very short, soft pubescence similar to an apricot. In comparison to its seed parent '119LT340' interspecific (non-patented) the fruit of the new variety has darker red skin color and is approximately 32 days later in maturity. In comparison to its pollen parent '53MB152' interspecific (non-patented) the fruit of the new variety has darker red skin color, yellow flesh compared to red and is approximately 30 days later in maturity. In comparison to the commercial variety 'Bella Royale' Interspecific (U.S. Plant Pat. No. 19,925) the fruit of the new variety is larger in size with darker red skin color.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year'old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices and climatic conditions.

*Vigor*.—Vigorous, tree growth of approximately 1.5 to 2 meters in height the first growing season. Varies slightly with soil type, fertility and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self-sterile, pollinator required.

*Density*.—Medium dense, usually pruned to vase shape to allow sunlight to center of tree to enhance fruit color and health of fruit wood.

*Hardiness*.—Hardy in all stone fruit growing areas of California. Tree grown in USDA Hardiness Zone 9. Winter chilling requirement approximately 800 hours at or below 45° F.

Trunk:

*Size*.—Average circumference 41.5 cm at 22.9 cm above ground on a 5 year old tree.

*Stocky*.—Medium stocky.

*Texture*.—Medium shaggy, roughness increases with age of tree.

*Color*.—Varies from 2.5Y 6/2 to 5Y 4/2.

Branches:

*Size*.—Medium. Average circumference 14.2 cm at 1.0 meter above ground on a 5 year old tree. Crotch angle approximately 30°, increases with heavy crop load.

*Surface texture*.—New growth relatively smooth. Mature growth medium rough, roughness increases with age.

*Lenticels*.—Average number 67 in a 25.8 sq cm section of branch. Average length 3.6 mm. Average width 1.7 mm. Color varies from 10YR 7/8 to 10YR 6/8.

*Color*.—New growth varies from 5GY 5/8 to 2.5YR 4/4 where exposed to the sun. Mature growth varies from 10YR 3/4 to 10YR 2/2, varies with age of growth.

Leaves:

*Size*.—Medium to large. Average length 116.3 mm. Average width 46.0 mm.

*Form*.—Oblanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins, glabrous. Lower surface relatively smooth except for ridges created by midrib and pinnate venation, glabrous.

*Petiole*.—Average length 14.9 mm. Average width 1.3 mm. Longitudinally grooved. Color varies from 5GY 6/6 to 7.5R 3/6. Surface — glabrous.

*Glands*.—Type — globose. Size — small to medium. Average length 1.0 mm. Average diameter 0.6 mm. Average number 2, varies 1 to 3. Located primarily on the base of the leaf blade and upper portion of the petiole. Color varies from 5GY 5/6 to 7.5R 2/6.

*Stipules*.—Average number 2. Average length 5.3 mm. Edges — pectinate. Color varies from 2.5GY 6/6 to 5GY 6/8.

*Color*.—Upper surface varies from 7.5GY 3/6 to 10GY 3/4. Lower surface varies from 7.5GY 5/4 to 7.5GY 5/6. Midvein color varies from 5GY 8/4 to 5GY 7/4.

Flower buds:

*Size*.—Small to medium. Average length 7.7 mm. Average diameter 4.6 mm.

*Hardiness*.—Hardy with respect to California winters.

*Form*.—Conical, becoming elongated just before opening.

*Pedicel*.—Average length 8.3 mm. Average width 0.6 mm. Color varies from 10Y 7/6 to 2.5GY 7/8. Surface — glabrous.

*Color*.—N 9.5/ (white).

*Number of buds per spur*.—Varies from 10 to 15, average number 12. Varies with age of spur.

Flowers:

*Blooming period*.—Date of First Bloom Feb. 23, 2012. Date of Petal Fall Mar. 5, 2012, varies slightly with climatic conditions.

*Size*.—Small to medium. Average height 10.4 mm. Average diameter 16.2 mm.

*Petals*.—Normally 5, alternately arranged to sepals. Petal apex — rounded. Petal base — rounded to somewhat truncated. Size — small to medium. Average length 7.9 mm. Average width 5.7 mm. Form — globose. Arrangement — free. Margin — sinuate. Color N 9.5/ (white). Both upper and lower surfaces glabrous.

*Sepals*.—Normally 5, alternately arranged to petals. Size — small. Average length 2.3 mm. Average width 1.7 mm. Form — triangular. Sepal apex rounded to triangular. Margin — entire. Both upper and lower surfaces glabrous. Color — upper surface varies from 10Y 7/8 to 2.5GY 7/6. Lower surface varies from 2.5GY 7/6 to 2.5GY 7/8.

*Stamens*.—Average number per flower 36. Average filament length 8.1 mm. On average, the stamens are above the height of the petals. Filament color N 9.5/ (white). Anther color varies from 2.5Y 8/2 to 7.5YR 5/10.

*Pollen*.—Present, self-sterile, pollinator required. Color varies from 2.5Y 7/10 to 5Y 7/10.

*Pistil*.—Normally one. Average length 7.7 mm. Position of stigma an average of 1.4 mm below anthers. Surface — pubescent. Color varies from 10Y 8/6 to 2.5GY 8/6.

*Fragrance*.—Heavy aroma.

*Color*.—N 9.5/ (white).

*Number flowers per flower bud*.—Average number 3, varies from 1 to 4.

*Pedicel*.—Average length 8.9 mm. Average width 0.6 mm. Color varies from 2.5GY 8/8 to 2.5GY 7/8. Surface glabrous.

Fruit:

*Maturity when described*.—Firm ripe and ready for consumption.

*Date of first picking*.—Aug. 2, 2012.

*Date of last picking*.—Aug. 10, 2012, varies slightly with climatic conditions.

*Size*.—Medium to large. Average diameter axially 60.8 mm. Average transversely in suture plane 62.8 mm. Average weight 150.5 grams, varies slightly with fertility of the soil, amount of thinning and climatic conditions.

*Form*.—Globose.

*Suture*.—Nearly smooth to very slightly lipped, extends from base to apex.

*Ventral surface*.—Nearly smooth.

*Apex*.—Slightly retuse.

*Base*.—Flat.

*Stem cavity*.—Rounded to slightly elongated in the suture plane. Average depth 1.7 mm. Average diameter 1.7 mm.

Stem:

*Size*.—Large. Average length 17.1 mm. Average diameter 1.9 mm.

*Color*.—Varies from 2.5GY 5/8 to 5GY 5/6.

Flesh:

*Ripens*.—Evenly.

*Texture*.—Firm, meaty.

*Fibers*.—Few, small, tender.

*Firmness*.—Good, comparable to other commercial interspecifics.

*Aroma*.—Slight.

*Amydgalin*.—Undetected.

*Eating quality*.—Excellent.

*Flavor*.—Excellent, good balance between acid and sugar.

*Juice*.—Moderate amount, enhances flavor.

*Acidity*.—Not available.

*Brix*.—Average Brix of 19.4°, varies slightly with amount of fruit per tree and climatic conditions.

*Color*.—Varies from 5Y 9/4 to 5Y 8.5/8.

*Pit cavity*.—Average length 26.0 mm. Average width 20.1 mm. Average depth 8.0 mm. Color varies from 7.5YR 6/10 to 7.5YR 6/12.

Skin:

*Thickness*.—Medium.

*Surface*.—Smooth.

*Pubescence*.—Moderate amount, very short.

*Bloom*.—Moderate amount, completely covered.

*Tendency to crack*.—None.

*Color*.—Ground color varies from 10YR 8/6 to 2.5Y 8.5/4. Overspread with 5R 2/4 to 7.5R 2/8.

*Tenacity*.—Tenacious to flesh.

*Astringency*.—Undetected.

Stone:

*Type*.—Freestone, weak adherence.

*Size*.—Medium to large. Average length 24.2 mm. Average width 19.0 mm. Average thickness 12.6 mm.

*Form*.—Ovoid.

*Base*.—Varies from flat to slightly pointed.

*Apex*.—Pointed. Average length 2.0 mm.

*Surface*.—Lightly pitted throughout, one short groove on each side of the suture extending from base to apex.

*Sides*.—Unequal, one side extending further from suture plane.

*Ridges*.—A small ridge on each side of suture extending from base to apex.

*Tendency to split*.—None.

*Color*.—Varies from 7.5YR 4/6 to 10YR 5/8 when dry.

Kernel:

*Size*.—Small to medium. Average length 15.0 mm. Average width 8.1 mm. Average thickness 3.9 mm.

*Form*.—Ovoid.

*Viability*.—Viable, complete embryo development.

*Skin color*.—Varies from 7.5YR 4/6 to 10YR 5/8.

Use:

*Dessert*.—Market — local and long distance.

Keeping quality: Good, held firm in cold storage for 2 weeks at 38° to 42° F. without internal breakdown of flesh or appreciable loss of flavor.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

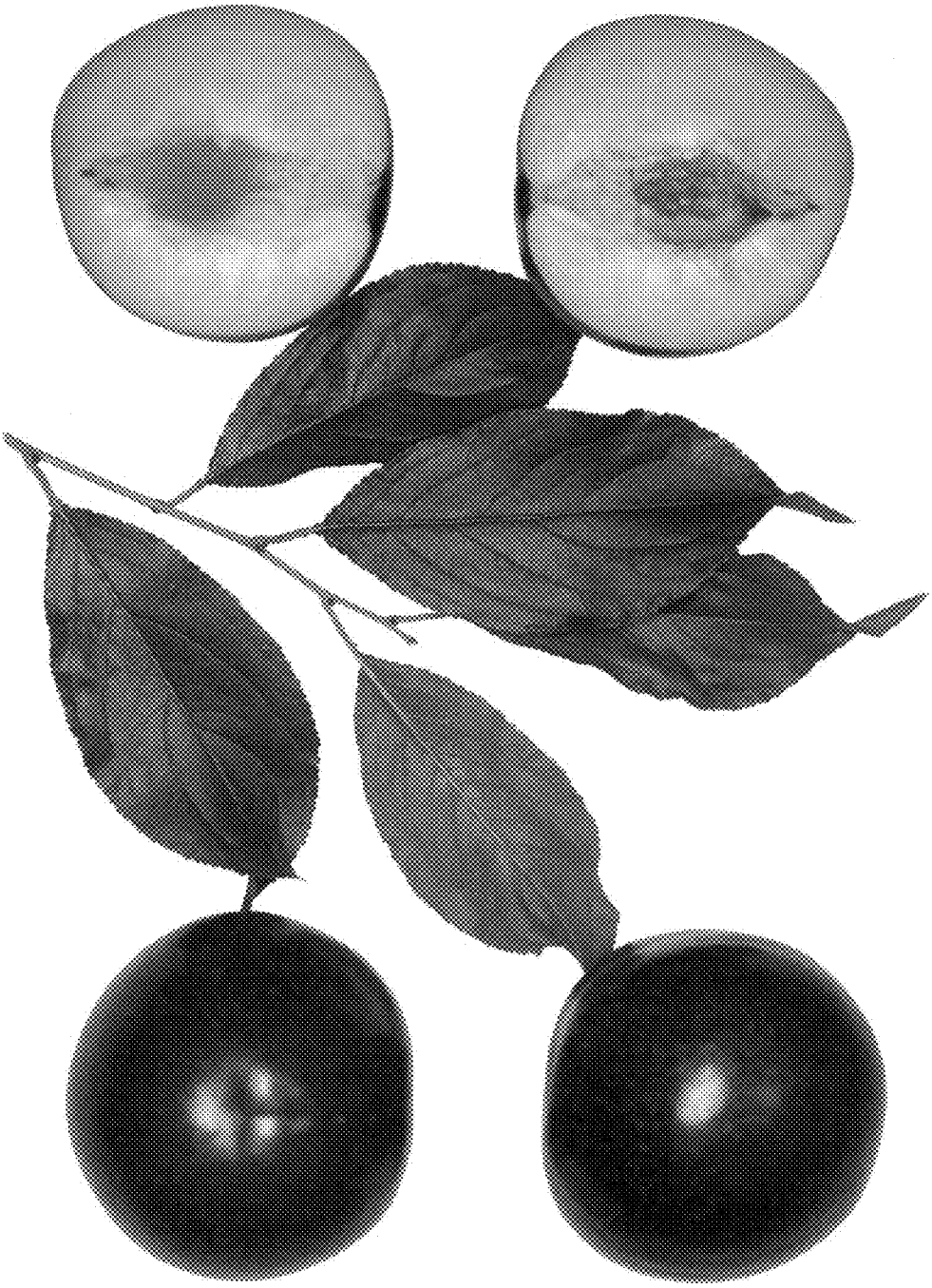

* * * * *